(12) United States Patent
Sato

(10) Patent No.: US 7,594,983 B2
(45) Date of Patent: Sep. 29, 2009

(54) ANALYTICAL TOOL

(75) Inventor: Yoshiharu Sato, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 572 days.

(21) Appl. No.: 10/533,601

(22) PCT Filed: Oct. 22, 2003

(86) PCT No.: PCT/JP03/13506

§ 371 (c)(1),
(2), (4) Date: Apr. 29, 2005

(87) PCT Pub. No.: WO2004/040288

PCT Pub. Date: May 13, 2004

(65) Prior Publication Data

US 2006/0049047 A1    Mar. 9, 2006

(30) Foreign Application Priority Data

Oct. 31, 2002    (JP)    ............................. 2002-318517

(51) Int. Cl.
*G01N 27/403* (2006.01)
*G01N 27/327* (2006.01)
(52) U.S. Cl. .................. 204/400; 204/403.01
(58) Field of Classification Search ........................ 204/403.01–403.15; 205/777.5, 778, 792; 422/55–58
See application file for complete search history.

(56) References Cited

U.S. PATENT DOCUMENTS

| 5,997,817 | A  | * | 12/1999 | Crismore et al. ......... 204/403.1 |
|---|---|---|---|---|
| 6,254,736 | B1 |   | 7/2001  | Earl et al. |
| 6,403,384 | B1 | * | 6/2002  | Lea ............................. 436/518 |
| 6,733,655 | B1 | * | 5/2004  | Davies et al. ............... 205/775 |
| 2003/0095897 | A1 | * | 5/2003  | Grate et al. ................. 422/186 |

FOREIGN PATENT DOCUMENTS

| EP | 1 314 978 | 5/2003 |
|---|---|---|
| JP | 2000-206077 | 7/2000 |
| JP | 2001-305093 | 10/2001 |
| JP | 2001-526388 | 12/2001 |
| JP | 2002-181757 | 6/2002 |
| WO | WO 02/10735 | 2/2002 |

\* cited by examiner

*Primary Examiner*—Alex Noguerola
(74) *Attorney, Agent, or Firm*—Hamre, Schumann, Mueller & Larson, P.C.

(57) ABSTRACT

The present invention relates to an analytical tool (1) including a capillary (5) for moving a sample liquid introduced through a liquid introduction port (51), and a window (43) for checking that the sample liquid of an amount necessary for measurement is supplied into the capillary (5). In the analytical tool (1), an opaque region (45) is defined between the liquid introduction port (51) and the window (43). For example, the analytical tool (1) includes a substrate (2), a cover (4) defining the capillary (5) together with the substrate (2), and a working electrode (21) and a counter electrode (22) which include respective exposed portions (21a, 22a) facing the interior of the capillary (5). Preferably, at least part of the window (43) is formed at a region which avoids a position directly above the exposed portions (21a, 22a).

16 Claims, 8 Drawing Sheets

ANALYTICAL TOOL

This application is a 371 of PCT/JP03/13506, filed Oct. 22, 2003.

TECHNICAL FIELD

The present invention relates to an analytical tool used for analyzing a particular component (such as glucose or cholesterol) contained in a sample liquid such as blood or urine.

BACKGROUND ART

Biosensors utilizing the capillary method are generally used for analyzing glucose contained in blood. For example, use is made of such a biosensor 6 as shown in FIGS. 9 and 10, which is formed with a window 61 for checking that a sample liquid is supplied into a capillary 60 (See JP-A 2001-526388, for example).

The capillary 60 is defined by a substrate 62, a spacer 63 and a cover 64. On the substrate 62, a working electrode 65 and a counter electrode 66 are formed. The working electrode 65 and the counter electrode 66 are covered by an insulating film 67 so that opposite ends 65a, 65b, 66a, 66b are exposed. The end 65a of the working electrode 65 and the end 66a of the counter electrode 66 are connected to each other by a reagent portion 68.

The window 61 is provided by forming a light-transmissive region in the cover 64. The window 61 extends continuously from a sample liquid introduction port 69a toward an air vent 69b and directly above the ends 65a, 66a of the working electrode 65 and the counter electrode 66.

In the biosensor 6, the sample liquid introduced through the sample liquid introduction port 69a moves in the capillary 60 toward the air vent 69b by capillary action. The movement of the sample liquid can be checked by visual inspection through the window 61 formed in the biosensor 6.

However, when the biosensor 6 is designed to analyze a small amount of sample, the width of the capillary 60 is set small. Further, the window 61 extends continuously from the sample liquid introduction port 69a toward the air vent 69b. Therefore, in the biosensor 6, it is sometimes difficult to check which point in the capillary 60 the sample liquid has reached. Therefore, it is not always easy for the user to check, by visual inspection, that the sample liquid has reached an intended point in the capillary 60. Further, when the insulating film 67 covering the working electrode 65 and the counter electrode 66 is colored, the color of the insulating film 67 makes the color of the sample liquid indistinctive. Also in such a case, the checking by visual inspection is difficult. Moreover, since the window 61 is formed to extend directly above the ends 65a, 66a of the working electrode 65 and the counter electrode 66, the internal structure of the biosensor 6, such as the working electrode 65 and the counter electrode 66, can be seen before the use of the sensor, which deteriorates the appearance.

DISCLOSURE OF THE INVENTION

An object of the present invention is to provide a biosensor which makes it possible to easily and reliably check, by visual inspection, whether or not a sample liquid has reached an intended point in a capillary without deteriorating the appearance.

According to the present invention, there is provided an analytical tool comprising a sample liquid introduction port, a capillary for moving a sample liquid introduced through the sample liquid introduction port, and a window for checking that the sample liquid of an amount necessary for measurement is supplied into the capillary. An opaque region is defined between the sample liquid introduction port and the window.

For example, the analytical tool further comprises a substrate, a cover bonded to the substrate and defining the capillary together with the substrate, and a working electrode and a counter electrode which are formed on the substrate and which include respective exposed portions facing the interior of the capillary. In this case, at least part of the window is formed at a region which avoids a position directly above the exposed portions. Preferably, the entirety of the window is formed at a region which avoids a position directly above the exposed portions.

The analytical tool of the present invention may further comprise an air vent for discharging air from the capillary. In this case, the window is provided between the air vent and a downstream one of the exposed portions in the flow direction of the sample liquid.

Preferably, the window includes a most upstream point which corresponds to or generally corresponds to a most downstream point of the downstream one of the exposed portions in a thickness direction of the substrate.

In the case where the analytical tool includes such a substrate and a cover as described above, the window is provided by forming a transparent portion in the cover and forming an opaque portion around the transparent portion.

For example, the cover comprises a transparent member, and an opaque layer formed with an opening and laminated on a surface of the transparent member. In this case, the window is defined by the opening.

The opaque layer may be provided by forming a film directly on the surface of the transparent member. Examples of method for the direct film formation of the opaque layer include gravure printing, screen printing, vapor deposition, sputtering and CVD. In the present invention, the direct film formation by gravure printing or screen printing is preferable. The opaque layer may comprise a thin film bonded to the surface of the transparent member. For example, such an opaque layer may be formed by bonding a colored film formed with an opening to the cover.

The cover may include an opaque member formed with an opening, and a transparent member embedded in the opening. In this case, the window is provided by the transparent member.

Preferably, the opaque region has a color which presents a high contrast with a color of a sample liquid such as blood or urine.

For example, the analytical tool of the present invention may further comprise an additional window for checking that introduction of the sample liquid into the capillary is started. The analytical tool may further comprise a working electrode and a counter electrode which are formed on the substrate and which include respective exposed portions facing the interior of the capillary. In this case, at least part of the additional window is formed at a region which avoids a position directly above the exposed portions.

Preferably, the entirety of the additional window is formed at a region which avoids a position directly above the exposed portions. For example, the additional window is provided between the sample liquid introduction port and an upstream one of the exposed portions in the flow direction of the sample liquid. For example, in this case, the additional window is provided adjacent to the sample liquid introduction port.

The additional window may be formed by a method which is similar to that for forming the window.

It is to be noted that the term "transparent" in the present invention indicates the state in which light is transmitted to a degree which makes it possible to check the sample liquid existing in the capillary so that the aim of the window can be attained and is not limited to the state in which 100% or close to 100% of visible light is transmitted.

BEST MODE FOR CARRYING OUT THE INVENTION

Figure 1:
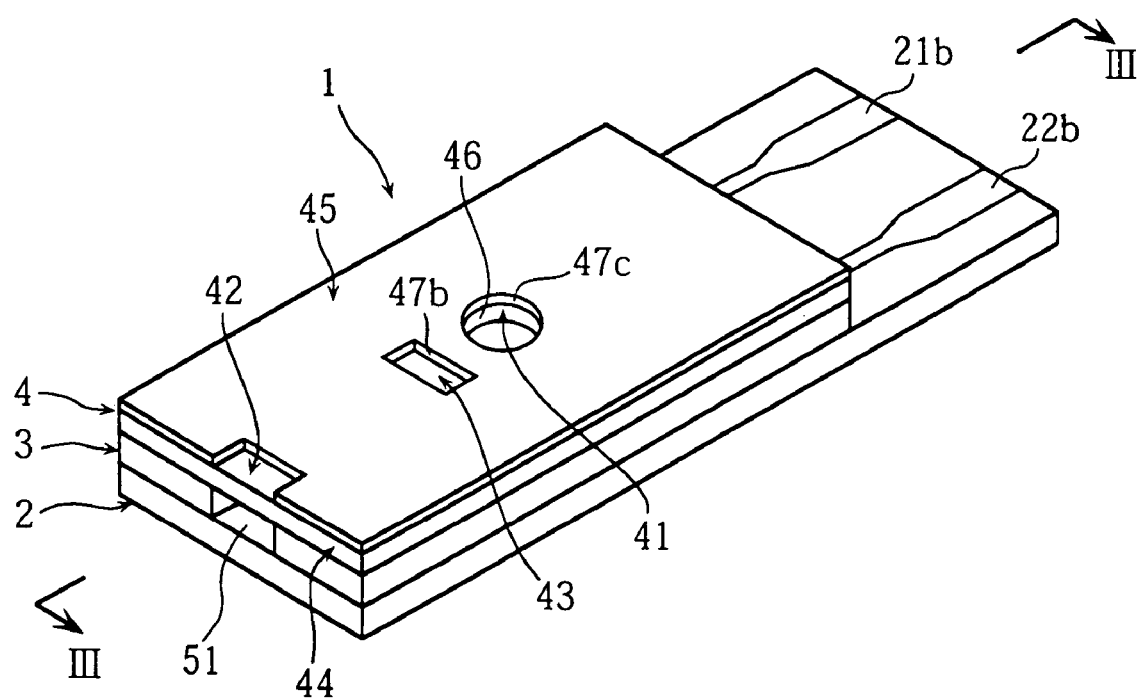
FIG. 1 is an entire perspective view showing a biosensor according to a first embodiment of the present invention.

A first and a second embodiments of the present invention will be described below in detail with reference to the drawings.

Firstly, the first embodiment of the present invention will be described with reference to FIGS. 1-5.

The biosensor 1 shown in FIGS. 1-4 is used for analyzing a particular component contained in a sample liquid such as blood or urine by an electrochemical method. The biosensor 1 includes a substrate 2, a spacer 3 and a cover 4, all of which define a capillary 5. The capillary 5 is utilized for moving a sample liquid from a sample liquid introduction port 51 toward an air vent 41.

Figure 2:
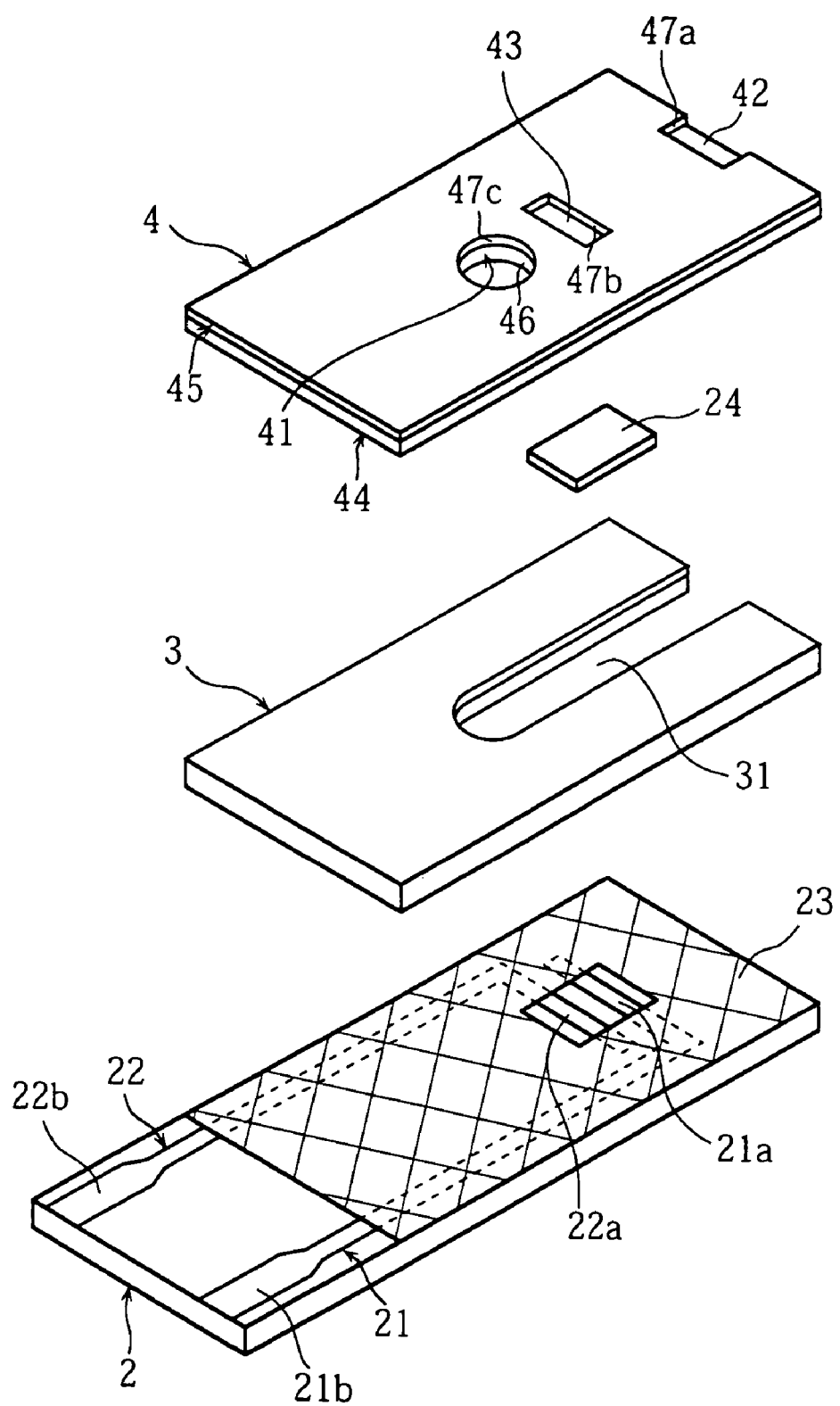
FIG. 2 is an exploded perspective view of the biosensor shown in FIG. 1.
Figure 3:
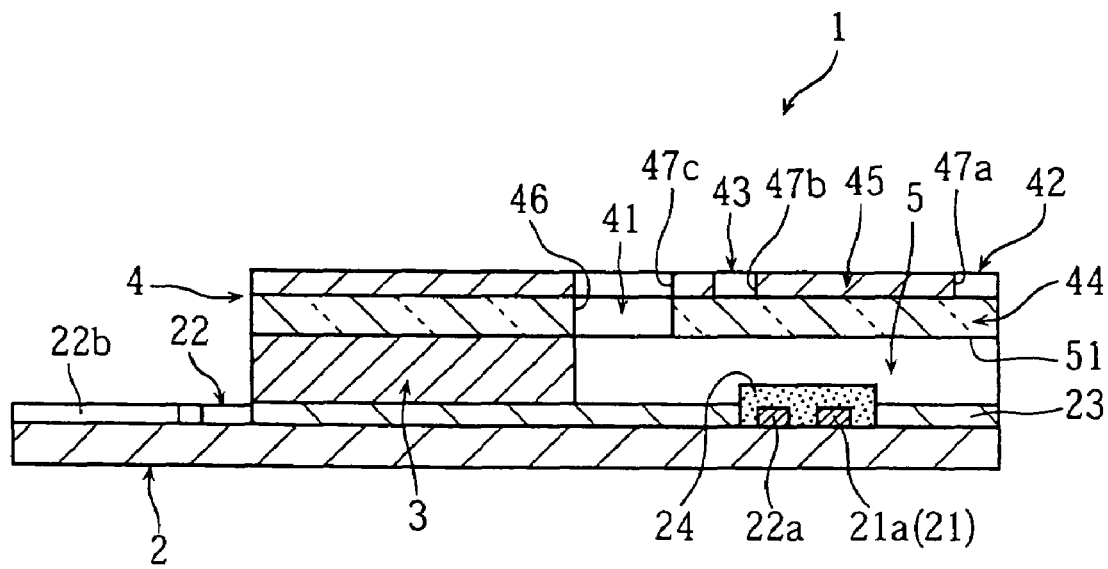
FIG. 3 is a sectional view taken along lines III-III in FIG. 1.
Figure 4:
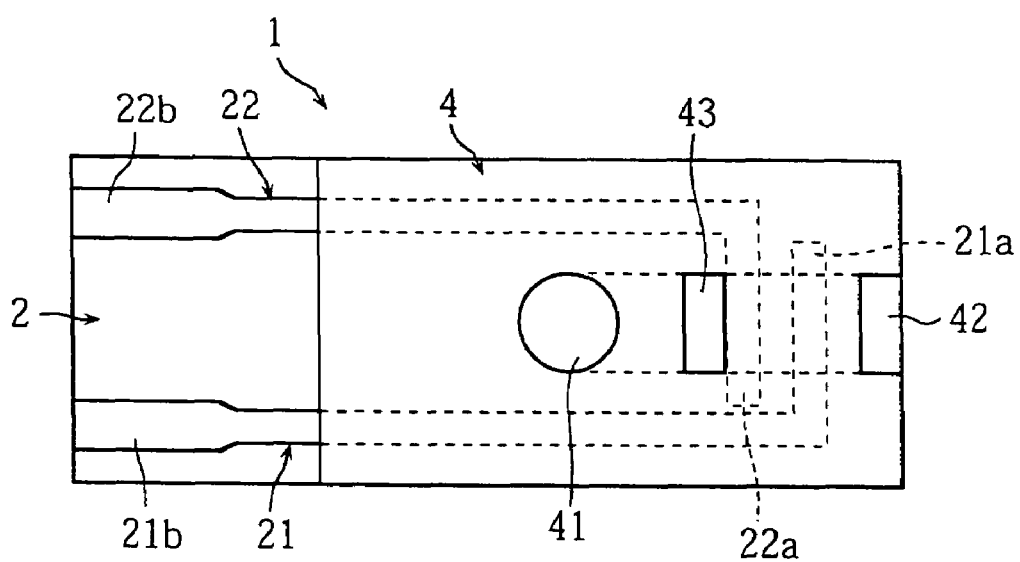
FIG. 4 is a plan view of the biosensor shown in FIG. 1.
Figure 5A:
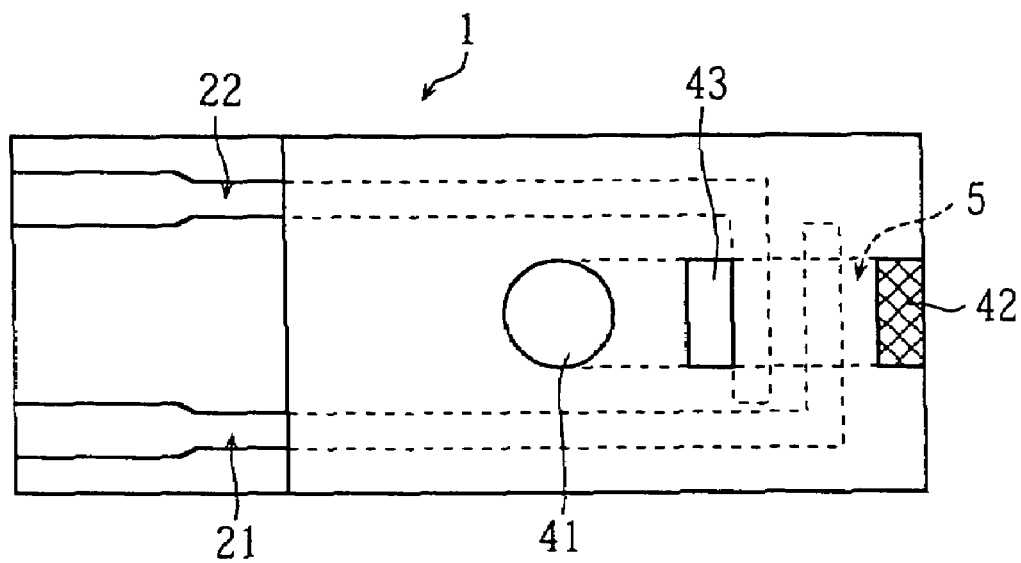
FIGS. 5A and 5B are plan views showing the introduction of a sample liquid into the capillary of the biosensor shown in FIG. 1.
Figure 5B:
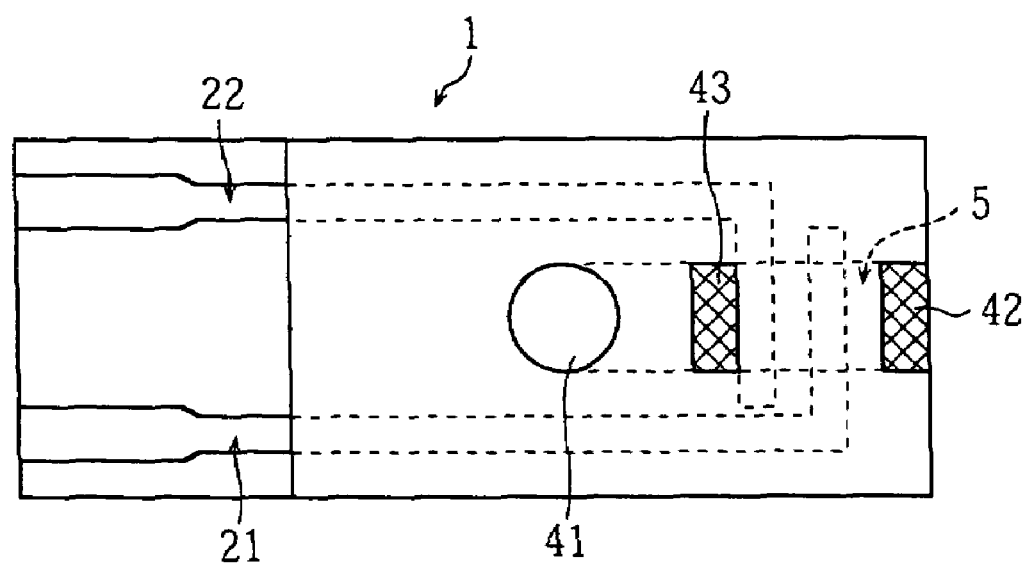

As better shown in FIGS. 2 and 3, the substrate 2 has an upper surface formed with a working electrode 21 and a counter electrode 22. The electrodes 21 and 22 are covered by an insulating film 23 so that respective opposite ends 21a, 21b, 22a, 22b are exposed. The ends 21a and 22a of the working electrode 21 and the counter electrode 22 are connected to each other by a reagent portion 24. For example, the reagent portion 24 is in a solid state and contains an oxidoreductase and an electron mediator. The kinds of oxidoreductase and electron mediator are selectable depending on the kind of the component to be measured. For example, to measure a glucose level, glucose dehydrogenase or glucose oxidase is used as the oxidoreductase, whereas potassium ferricyanide is used as the electron mediator.

The spacer 3 serves to define the height of the interior of the capillary 5. The spacer 3 is formed with a slit 31 having an open front end. The slit 31 serves to define the width of the interior of the capillary 5. The open front end of the slit 31 constitutes the sample liquid introduction port 51 for introducing a sample liquid into the capillary 5.

As shown in FIGS. 1 through 3, the cover 4 includes an air vent 41 and two windows 42 and 43. The air vent 41 serves to discharge air in the capillary 5 to the outside and communicates with the interior of the capillary 5. The window 42 is utilized for checking whether or not the introduction of sample liquid into the capillary 5 is started and also serves as a mark for introducing the sample liquid through the sample liquid introduction port 51. The window 43 is utilized for checking the movement of the sample liquid in the capillary 5 and provided on the side of the air vent 41 which is closer to the sample liquid introduction port 51. As better shown in FIGS. 3 and 4, the windows 42 and 43 are so arranged as to avoid the positions directly above the working electrode 21 and the counter electrode 22, and the upstream edge of the window 43 generally corresponds to the downstream edge of the end 22a of the counter electrode 22 in the thickness direction of the substrate 2.

The cover 4 comprises a transparent member 44 and an opaque layer 45 laminated thereon. The transparent member 44 includes a through-hole 46 constituting the air vent 41 and is entirely formed of a transparent resin, for example.

The opaque layer 45 includes three openings 47a-47c. The opening 47a constitutes the window 42 and is provided adjacent the sample liquid introduction port 51. The opening 47b constitutes the window 43 and is provided directly above the capillary 5 and between the opening 47c (air vent 41) and the ends 21a, 22a of the working electrode 21 and the counter electrode 22. The opening 47c constitutes the air vent 41 and provided at a location corresponding to the through-hole 46 of the transparent member 44.

The opaque layer 45 may be provided by forming a film directly on the upper surface of the transparent member 44. Such film formation of the opaque layer 45 may be performed by gravure printing, screen printing, vapor deposition, sputtering or CVD, for example. In view of the manufacturing cost, gravure printing or screen printing is preferable. In gravure printing or screen printing, the opaque layer 45 is formed by applying ink containing pigment or paint on the upper surface of the transparent member 44 and then drying. As the pigment, it is preferable to use pigment of a color which presents a high contrast with the color of the sample liquid. The opaque layer 45 may be made by bonding a colored film on the upper surface of the transparent member.

In the biosensor 1, when a sample liquid is introduced through the sample liquid introduction port 51, the sample liquid moves toward the air vent 41 by capillary action. The introduction of the sample liquid can be easily and reliably performed by utilizing the window 42 as a mark. Whether or not the sample liquid is introduced into the capillary 5 can be determined by whether or not the color viewed through the window 42 is changed, as indicated by cross-hatching in FIG. 5A. Whether or not the sample liquid of an amount necessary for the measurement is supplied into the capillary 5, i.e., whether or not the surfaces of the working electrode 21 and the counter electrode 22 are wetted by the sample liquid, for example, can be determined by whether or not the color viewed through the window 43 is changed, as indicated by cross-hatching in FIG. 5B.

As the sample liquid moves, the reagent portion 24 is dissolved by the sample liquid. As a result, a liquid phase reaction system is established in the capillary 5. In the liquid phase reaction system, oxidation/reduction reaction occurs to produce a reaction product of an amount related with the amount of the measurement target component. By applying a voltage to the liquid phase reaction system using the working electrode 21 and the counter electrode 22, the amount of the reaction product can be found out as a responsive current corresponding to the amount of the reaction product, for example. Based on the responsive current, the amount of the measurement target component can be computed.

In the biosensor 1, based on the color change observed through the windows 42 and 43, it is possible to easily and reliably check, by visual inspection, that the introduction of the sample liquid into the capillary 5 is started or the sample liquid of an amount necessary for the measurement is supplied into the capillary 5. Particularly, when the color around the windows 42, 43 presents a high contrast with the color of the sample liquid, the introduction of the sample liquid into the capillary 5 and the reaching of the sample liquid to an intended position can be checked more easily and reliably. The windows 42 and 43 are so formed as to avoid the positions directly above the working electrode 21 and the counter electrode 22, and the proportion of the area of the windows 42 and 43 to the obverse surface of the cover 4 is relatively small. Therefore, the internal area of the biosensor 1 which can be viewed from the outside through the windows 42 and 43 is relatively small, and the working electrode 21 and the counter electrode 22 cannot be seen through the cover 4. Therefore, the appearance of the biosensor 1 can be improved.

Figure 6A:
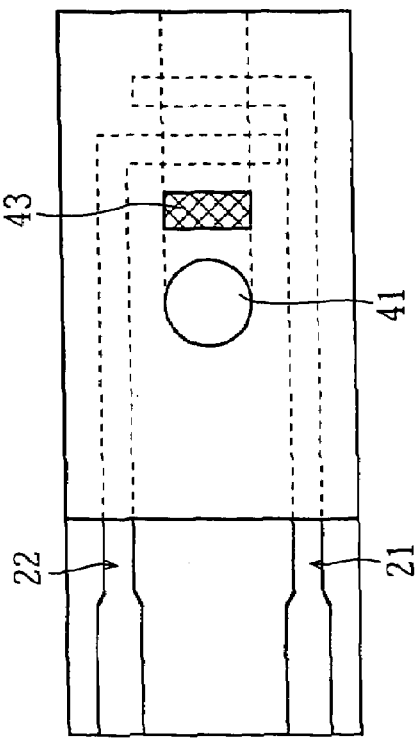
FIGS. 6A-6D are plan views showing other examples of biosensor according to the present invention.
Figure 6B:
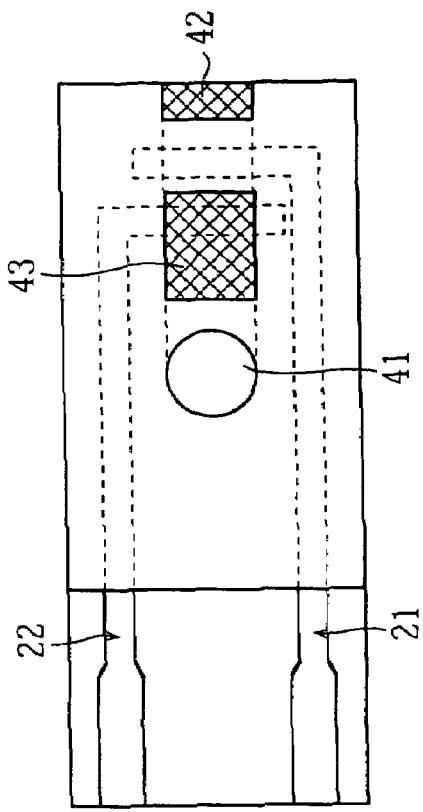
Figure 6C:
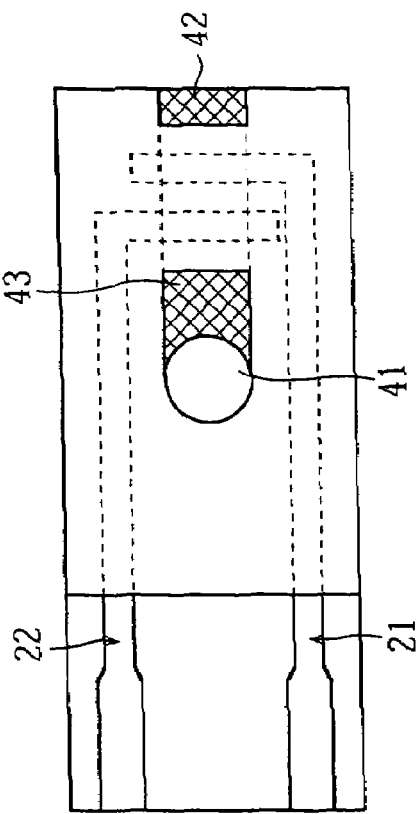
Figure 6D:
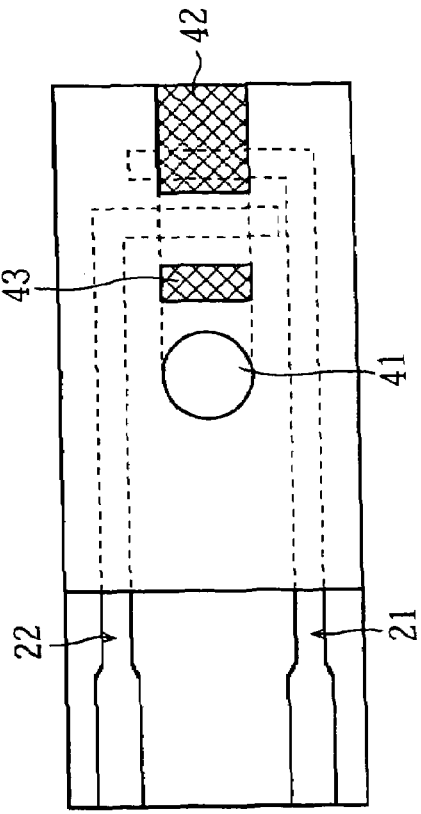

For example, the windows of the biosensor may have such structures as shown in FIGS. 6A-6D. Specifically, as shown in FIG. 6A, the window 43 may be connected to the air vent 41. As shown in FIG. 6B, the window 42 may be dispensed with. As shown in FIG. 6C, the window 42 may be extended directly above the working electrode 21. As shown in FIG. 6D, the window 43 may be extended directly above the counter electrode 22. Also in these examples shown in the figures, the portion on the side of the window 43 which is closer to the sample liquid introduction port 51 is made opaque, and the windows 42 and 43 are so formed as to avoid the position directly above at least one of the working electrode 21 and the counter electrode 22. Therefore, the biosensors of these examples can enjoy the same advantages as those of the above-described biosensor 1.

Figure 7:
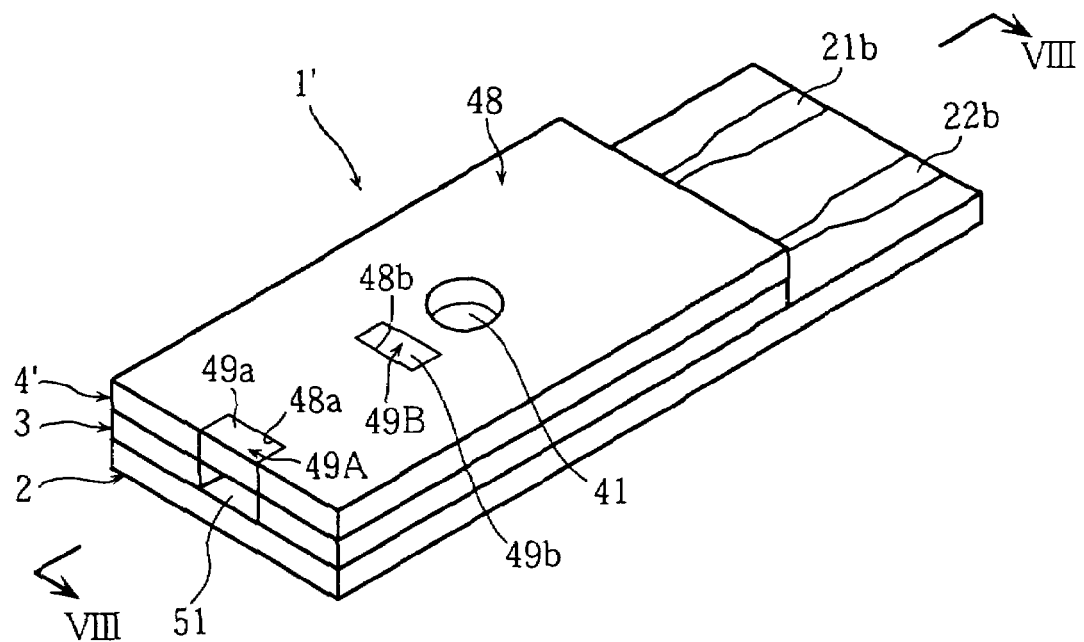
FIG. 7 is an entire perspective view of a biosensor according to a second embodiment of the present invention.
Figure 8:
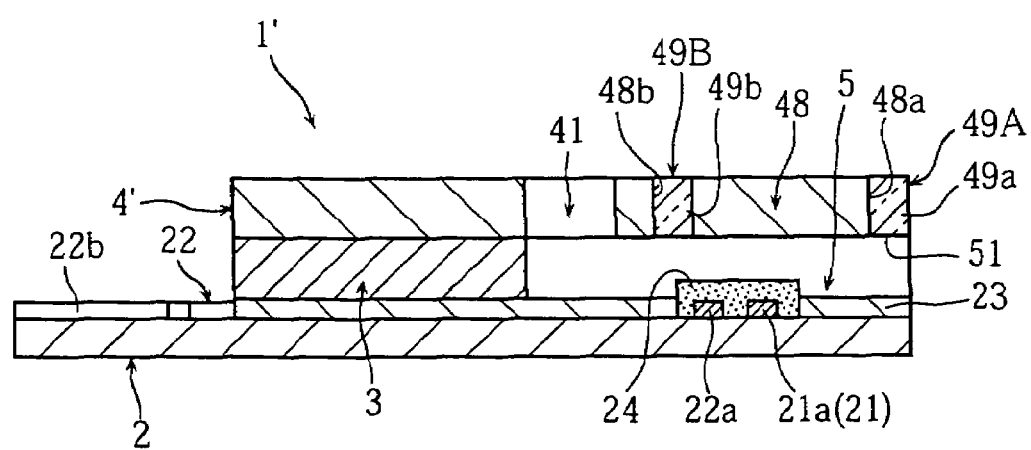
FIG. 8 is a sectional view taken along lines VIII-VIII in FIG. 7.
Figure 9:
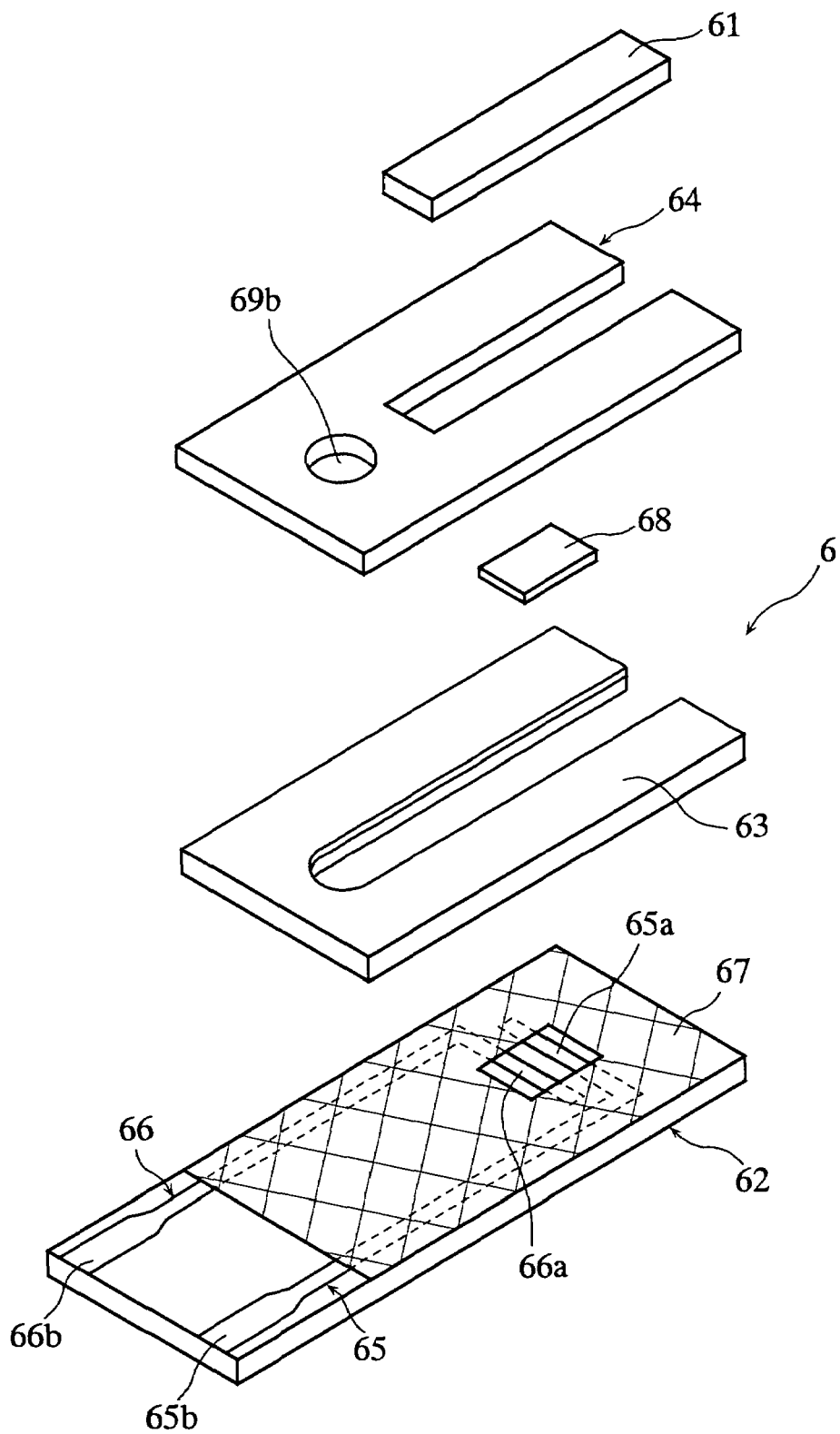
FIG. 9 is an exploded perspective view of an example of prior art biosensor.
Figure 10:
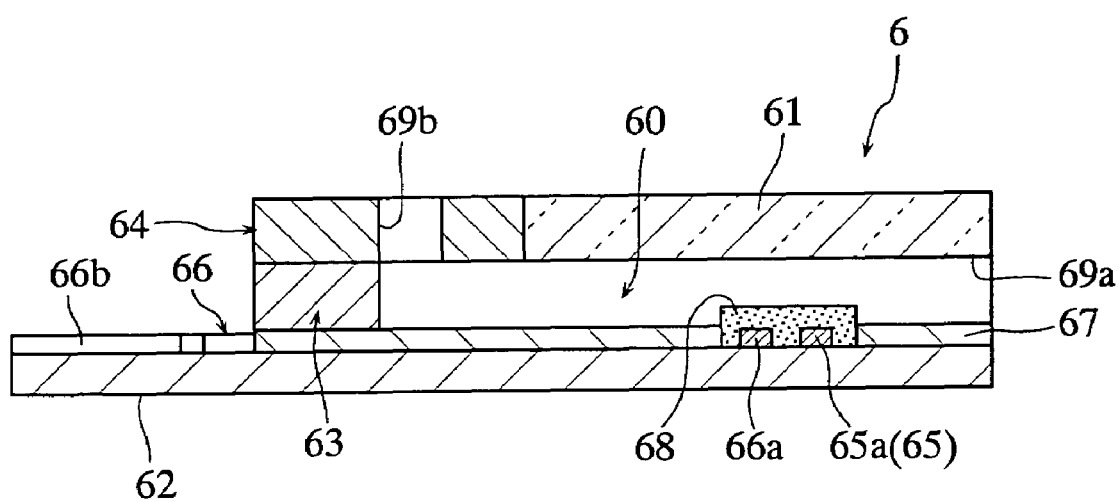
FIG. 10 is a sectional view of the biosensor shown in FIG. 9.

Referring to FIGS. 7 and 8, a biosensor according to the second embodiment of the present invention will be described. In these figures, the elements which are identical or similar to those of the biosensor 1 are designated by the same reference signs, and the description thereof is omitted.

In the biosensor 1', the cover 4' is made up of two kinds of members. Specifically, the cover 4' includes an opaque element 48 formed with openings 48a, 48b, and transparent elements 49a, 49b embedded in the openings 48a, 48b. The transparent 49a, 49b constitute windows 49A, 49B.

In the biosensor 1' again, based on the color change which can be observed through the windows 49A and 49B, it is possible to easily and reliably check whether the introduction of the sample liquid into the capillary 5 is started or whether the sample liquid of an amount necessary for the measurement is supplied into the capillary 5. Moreover, since the internal structure of the biosensor 1' is not easily visible, the biosensor 1 has a good appearance.

Similarly to the biosensor 1, the windows 49A, 49B of the biosensor 1' can also be modified in such ways as described with reference to FIGS. 6A-6D.

The present invention is not limited to the foregoing embodiments and may be modified in many ways. For example, although the capillary of the analytical tool in each of the foregoing embodiments is defined by the substrate, the spacer and the cover, the present invention is also applicable to an analytical tool in which a capillary is defined by a substrate formed with a recess, and a cover. The present invention is not limited to an analytical tool for performing analysis by an electrochemical method and is also applicable to an analytical tool for performing analysis by an optical method.

The invention claimed is:

1. An analytical tool comprising:
   a substrate,
   a cover bonded to the substrate,
   a capillary formed between the substrate and the cover for moving a sample liquid from a sample liquid introduction port toward an air vent,
   a first electrode formed on the substrate and having a first end located in the capillary,
   a second electrode formed on the substrate and having a second end located in the capillary downstream from the first end of the first electrode with respect to a flow direction of the sample liquid, and
   a window formed in the cover for checking whether the sample liquid is supplied into the capillary,
   wherein the window has a downstream edge located downstream from the second end of the second electrode to check whether the sample liquid is supplied beyond the second end of the second electrode, and
   wherein the window is formed at a region which avoids a position directly above the second end of the second electrode.

2. The analytical tool according to claim 1, wherein entirety of the window is formed at a region which avoids a position directly above the second end of the second electrode.

3. The analytical tool according to claim 2,
   wherein the window is provided between the air vent and the second end of the second electrode in the flow direction of the sample liquid.

4. The analytical tool according to claim 3, wherein the window includes an upstream edge which is aligned with a downstream edge of the second end of the second electrode in a thickness direction of the substrate.

5. An analytical tool comprising:
   a substrate,
   a cover bonded to the substrate,
   a capillary formed between the substrate and the cover for moving a sample liquid from a sample liquid introduction port toward an air vent,
   a first electrode formed on the substrate and having a first end located in the capillary,
   a second electrode formed on the substrate and having a second end located in the capillary downstream from the first end of the first electrode with respect to a flow direction of the sample liquid, and
   a window formed in the cover for checking whether the sample liquid is supplied into the capillary,
   wherein the window has a downstream edge located downstream from the second end of the second electrode to check whether the sample liquid is supplied beyond the second end of the second electrode, and
   wherein the window is provided by forming a transparent portion in the cover and forming an opaque portion around the transparent portion.

6. The analytical tool according to claim 5, wherein the cover comprises a transparent member, and an opaque layer formed with an opening and laminated on a surface of the transparent member;
   wherein the window is defined by the opening.

7. The analytical tool according to claim 6, wherein the opaque layer is provided by forming a film directly on the surface of the transparent member.

8. The analytical tool according to claim 6, wherein the opaque layer comprises a film bonded to the surface of the transparent member.

9. The analytical tool according to claim 5, wherein the cover includes an opaque member formed with an opening, and a transparent member embedded in the opening; and
    wherein the window is provided by the transparent member.

10. An analytical tool comprising:
    a substrate,
    a cover bonded to the substrate,
    a capillary formed between the substrate and the cover for moving a sample liquid from a sample liquid introduction port toward an air vent,
    a first electrode formed on the substrate and having a first end located in the capillary,
    a second electrode formed on the substrate and having a second end located in the capillary downstream from the first end of the first electrode with respect to a flow direction of the sample liquid, and
    a window formed in the cover for checking whether the sample liquid is supplied into the capillary,
    wherein the window has a downstream edge located downstream from the second end of the second electrode to check whether the sample liquid is supplied beyond the second end of the second electrode, and
    wherein the opaque region has a color which presents a contrast with a color of the sample liquid.

11. The analytical tool according to claim 10, wherein the sample liquid is blood or urine.

12. An analytical tool comprising:
    a substrate,
    a cover bonded to the substrate,
    a capillary formed between the substrate and the cover for moving a sample liquid from a sample liquid introduction port toward an air vent,
    a first electrode formed on the substrate and having a first end located in the capillary,
    a second electrode formed on the substrate and having a second end located in the capillary downstream from the first end of the first electrode with respect to a flow direction of the sample liquid, and
    a window formed in the cover for checking whether the sample liquid is supplied into the capillary,
    wherein the window has a downstream edge located downstream from the second end of the second electrode to check whether the sample liquid is supplied beyond the second end of the second electrode, and
    wherein the analytical tool further comprises an additional window for checking whether introduction of the sample liquid into the capillary is started.

13. The analytical tool according to claim 12,
    wherein at least part of the additional window is formed at a region which avoids a position directly above the first end of the first electrode.

14. The analytical tool according to claim 13, wherein entirety of the additional window is formed at a region which avoids a position directly above the first end of the first electrode.

15. The analytical tool according to claim 14, wherein the additional window is provided between the sample liquid introduction port and the first end of the first electrode in the flow direction of the sample liquid.

16. The analytical tool according to claim 15, wherein the additional window is provided adjacent to the sample liquid introduction port.

* * * * *

UNITED STATES PATENT AND TRADEMARK OFFICE
CERTIFICATE OF CORRECTION

PATENT NO. : 7,594,983 B2
APPLICATION NO. : 10/533601
DATED : September 29, 2009
INVENTOR(S) : Yoshiharu Sato It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1047 days.

Signed and Sealed this

Twenty-eighth Day of September, 2010

David J. Kappos
*Director of the United States Patent and Trademark Office*